(12) United States Patent
Henry et al.

(10) Patent No.: US 8,480,874 B2
(45) Date of Patent: Jul. 9, 2013

(54) GEL CASSETTE ADAPTOR

(75) Inventors: Adam S. Henry, Oceanside, CA (US); Tom R. Jackson, La Jolla, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 12/873,029

(22) Filed: Aug. 31, 2010

(65) Prior Publication Data

US 2011/0089035 A1    Apr. 21, 2011

Related U.S. Application Data

(63) Continuation of application No. 11/404,364, filed on Apr. 14, 2006.

(60) Provisional application No. 60/671,756, filed on Apr. 15, 2005, provisional application No. 60/706,084, filed on Aug. 5, 2005.

(51) Int. Cl.
*G01N 27/453* (2006.01)

(52) U.S. Cl.
USPC ........... 204/606; 204/600; 204/616; 204/620

(58) Field of Classification Search
USPC ................. 204/450, 456, 465–467, 600, 605, 204/606, 615, 616–619
See application file for complete search history.

(56) References Cited

U.S. PATENT DOCUMENTS

| | | | |
|---|---|---|---|
| 5,112,470 A | | 5/1992 | Sylvester |
| 5,186,807 A | * | 2/1993 | Sanford et al. ............... 204/618 |
| 5,543,023 A | * | 8/1996 | Lugojan ....................... 204/618 |
| 5,562,813 A | * | 10/1996 | Mullaart et al. ............. 204/618 |
| 6,001,233 A | | 12/1999 | Levy |
| 6,027,628 A | | 2/2000 | Yamamura et al. |
| 6,413,402 B1 | * | 7/2002 | Manusu et al. ............... 204/620 |
| 6,416,644 B1 | | 7/2002 | Anderson et al. |
| 6,436,262 B1 | * | 8/2002 | Perez ............................ 204/618 |
| 6,451,193 B1 | * | 9/2002 | Fernwood et al. ............ 204/618 |
| 2001/0037940 A1 | | 11/2001 | Shih et al. |
| 2003/0106798 A1 | | 6/2003 | Seabrook et al. |

FOREIGN PATENT DOCUMENTS

| | | |
|---|---|---|
| EP | 0339972 | 11/1989 |
| WO | WO-2006/113694 | 10/2006 |

OTHER PUBLICATIONS

International Report on Patentability mailed on Oct. 16, 2007 in PCT/US06/14529.
International Search Report mailed on Oct. 23, 2006 in PCT/US06/14529.
Written Opinion mailed on Oct. 15, 2007 in PCT/US06/14529.
U.S. Appl. No. 11/404,364; Office action mailed Mar. 18, 2011.

* cited by examiner

*Primary Examiner* — Luan Van
*Assistant Examiner* — Gurpreet Kaur (57) ABSTRACT

A gel cassette adaptor for use with an electrophoresis system gel cassette is disclosed herein. The gel cassette adaptor allows a single gel cassette to be compatible with more than one electrophoresis system. In one example embodiment, the gel cassette adaptor includes an open sided trough having an attachment perimeter and an attachment flange coupled to the attachment perimeter. The attachment flange is designed to be compatible for mating with a gel cassette that is compatible with a first electrophoresis system. After attachment of the gel cassette adaptor, the resulting gel cassette assembly is compatible with a second electrophoresis system. Also provided is a gel cassette that includes a stabilizer post that connects the cassette plates to maintain a constant gap width between the plates during electrophoresis. In reducing deformation of the gap space between plates during gel runs, the stabilizer post can improve electrophoresis results for wide format gels.

14 Claims, 7 Drawing Sheets

GEL CASSETTE ADAPTOR

CROSS-REFERENCE TO RELATED APPLICATION

This application is a continuation and claims the right of priority under 35 U.S.C §120 to U.S. application Ser. No. 11/404,364, filed Apr. 14, 2006, which claims the benefit of U.S. Provisional Application Ser. No. 60/671,756, filed on Apr. 15, 2005, and U.S. Provisional Application Ser. No. 60/706,084, filed on Aug. 5, 2005, all of which are commonly assigned with the instant application, and the disclosures of all of which are hereby expressly incorporated by reference in their entirety as though fully set forth herein.

TECHNICAL FIELD

The present invention relates generally to gel cassettes for use in an electrophoresis system. More particularly, the present invention relates to an adaptor for use with a gel cassette to make it compatible with more than one electrophoresis system, and a gel cassette stabilizer post to maintain a uniform gap between gel plates during electrophoresis.

BACKGROUND

Gel electrophoresis is commonly used to separate by molecular size biological molecules, such as deoxyribonucleic acid ("DNA"), ribonucleic acid ("RNA") and proteins. To perform gel electrophoresis, a polymeric gel, such as polyacrylamide, is formed between spaced glass or plastic plates; this assembly is known as a gel cassette. The gel cassette is then placed in a container along with anode and cathode elements at the top and bottom of the gel. Sample wells formed in the top of the gel are filled with buffer solutions. Molecule samples prepared in a sample buffer that may contain a tracking dye are then placed in the wells. Electrophoretic buffer solutions containing conductive ions are added to the container to make electrical contact between the gel, the samples in the wells and the anode and cathode elements. A voltage is then applied across the gel, which causes the sample molecules and any tracking dye to migrate toward the bottom of the gel, and separate into bands whose migration distance depends on molecular size.

Typically, each electrophoresis system requires the use of a unique gel cassette that is only compatible with that particular system. These unique cassettes are expensive and the user may be limited in the type of gels available for that unique cassette. Accordingly, it is desirable to provide a gel cassette that may be adaptable for use with more than one electrophoresis system. In addition, it is desirable to provide a gel cassette that is simple to convert to the desired cassette configuration. Furthermore, other desirable features and characteristics of the present invention will become apparent from the subsequent detailed description and the appended claims, taken in conjunction with the accompanying drawings and the foregoing technical field and background.

SUMMARY OF THE INVENTION

The present invention relates to a gel cassette adaptor that is designed to be attached to a gel cassette. This allows the gel cassette to be compatible with more than one electrophoresis system. For some electrophoresis systems, the gel cassette is used without the adaptor. For other electrophoresis systems, the gel cassette adaptor is attached to gel cassette to form a gel cassette assembly with an upper buffer chamber, which is required by some electrophoresis systems. In certain embodiments such gel cassette adaptors are for single use, whereas in other embodiments such gel cassette adaptors are for multiple use.

A gel cassette adaptor is disclosed for use with a gel cassette. An aspect disclosed herein are gel cassette assemblies which include a gel cassette; and a gel cassette adaptor. In certain embodiments of the gel cassette adaptors described herein are gel cassette adaptors which include an open sided trough having an attachment perimeter; and an attachment flange coupled to the attachment perimeter, wherein the attachment flange is configured for compatible mating with a gel cassette. In embodiments of this aspect, the trough is between 2 to 10 inches wide×0.5 to 4.0 inch in height×0.5 and 4.0 inches deep, while in further or alternative embodiments, the trough is between 4 to 8 inches wide×0.75 to 2.0 inch in height×0.75 and 2.0 inches deep. In a further or alternative embodiment, the trough is approximately 5.4 inches wide× 1.3 inches in height×1.1 inches deep. In further or alternative embodiments, the trough has a volume capacity between about 10 and about 600 mL. In further or alternative embodiments, the trough has a volume capacity between about 20 and about 400 mL. In further or alternative embodiments, the trough has a volume capacity between about 30 and about 300 mL. In further or alternative embodiment, the trough has a volume capacity between 10 and 250 mL. In further or alternative embodiments, the trough has a volume capacity between about 50 and about 100 mL. In further or alternative embodiments, the gel cassette adaptor includes an adhesive positioned on the attachment flange wherein the adhesive is configured to facilitate attachment of the gel cassette adaptor to the gel cassette. In another or alternative embodiment, the adhesive is pressure sensitive tape. In other or alternative embodiments, the attachment flange is integral with the open sided trough, thereby creating a unitary structure. In further or alternative embodiments, the gel cassette adaptor also includes one or more alignment elements that interact with one or more corresponding features on the gel cassette to facilitate proper positioning of the gel cassette adaptor relative to the gel cassette.

In further or alternative embodiments, the gel cassette adaptor, the open sided trough, the attachment flange and the unitary structure may be made of plastic, whereas in further or alternative embodiments the plastic is selected from the group consisting of styrene acrylonitrile, polycarbonate, polystyrene, acrylic based polymers, polymethyl methacrylate, polyethylene terephthalate, glycol-modified polyethylene terephthalate, polypropylene, Acetel and copolymers thereof. In further or alternative embodiments, the gel cassette adaptor, the open sided trough, the attachment flange and the unitary structure may be fabricated using molding techniques, hot embossing methods, casting processes, thermoforming methods, stereolithography processes, machining methods and milling processes. In further or alternative embodiments, such molding techniques include injection molded and compression molding.

In another aspect disclosed herein are gel cassette kits. The kit includes a gel cassette and a gel cassette adaptor. The gel cassette is designed for use with a first electrophoresis system (and it may be incompatible with a second electrophoresis system), and the gel cassette adaptor is designed to convert the gel cassette into a gel cassette assembly that is compatible with the second electrophoresis system. In further or alternative embodiments, such gel cassette kit include a gel cassette; and a gel cassette adaptor configured for attachment to the gel cassette to form a single-use upper buffer chamber, while in further or alternative embodiments, such kits also include an adhesive element configured to facilitate attachment of the gel cassette adaptor to the gel cassette. In a further or alternative embodiment, the adhesive is pressure sensitive tape. In further or alternative embodiments of such kits, the gel cassette adaptor is made of plastic. In further or alternative embodiments, the plastic is an injection molded plastic, while in further or alternative embodiments, the plastic is a thermoformed plastic. In still further or alternative embodiments, the plastic is selected from styrene acrylonitrile, polycarbonate, polystyrene, acrylic based polymers, polymethyl methacrylate, polyethylene terephthalate, glycol-modified polyethylene terephthalate, polypropylene, Acetel and copolymers thereof. In further or alternative embodiments of such kits, the gel cassette adaptor includes an open sided trough having an attachment perimeter; and an attachment flange coupled to the attachment perimeter, the attachment flange being configured for compatible mating with the gel cassette. In further or alternative embodiments of such kits, the gel cassette adaptor also includes one or more alignment elements that interact with one or more corresponding features on the gel cassette to facilitate proper positioning of the gel cassette adaptor relative to the gel cassette. In further or alternative embodiments of such kits, the gel cassette is compatible for use with a first electrophoresis system and is incompatible for use with a second electrophoresis system and attachment of the gel cassette adaptor to the gel cassette creates a gel cassette assembly that is compatible for use with the second electrophoresis system.

In another aspect disclosed herein are kits which include a plurality of gel cassette adaptors. In further or alternative embodiments, such gel cassette adaptors include an open sided trough having an attachment perimeter; and an attachment flange coupled to the attachment perimeter, the attachment flange being configured for compatible mating with a gel cassette. In embodiments of this aspect, the trough is between 2 to 10 inches wide×0.5 to 4.0 inch in height×0.5 and 4.0 inches deep, while in further or alternative embodiments, the trough is between 4 to 8 inches wide×0.75 to 2.0 inch in height×0.75 and 2.0 inches deep. In a further or alternative embodiment, the trough is approximately 5.4 inches wide× 1.3 inches in height×1.1 inches deep. In further or alternative embodiments, the trough has a volume capacity between about 10 and about 600 mL. In further or alternative embodiments, the trough has a volume capacity between about 20 and about 400 mL. In further or alternative embodiments, the trough has a volume capacity between about 30 and about 300 mL. In further or alternative embodiment, the trough has a volume capacity between 10 and 250 mL. In further or alternative embodiments, the trough has a volume capacity between about 50 and about 100 mL. In further or alternative embodiments, the gel cassette adaptors also include an adhesive positioned on the attachment flange, the adhesive being configured to facilitate attachment of the gel cassette adaptor to the gel cassette. In a further or alternative embodiment, the adhesive is pressure sensitive tape. In further or alternative embodiments of such kits, the gel cassette adaptor is made of plastic. In further or alternative embodiments, the plastic is an injection molded plastic, while in further or alternative embodiments, the plastic is a thermoformed plastic. In still further or alternative embodiments, the plastic is selected from styrene acrylonitrile, polycarbonate, polystyrene, acrylic based polymers, polymethyl methacrylate, polyethylene terephthalate, glycol-modified polyethylene terephthalate, polypropylene, Acetel and copolymers thereof. In further or alternative embodiments, the gel cassette adaptors also include one or more alignment elements that interact with one or more corresponding features on the gel cassette to facilitate proper positioning of the gel cassette adaptor relative to the gel cassette.

In another aspect are methods of using a gel cassette adaptors described herein. In further or alternative embodiments of such methods, the method involves obtaining a gel cassette designed for compatible use with a first electrophoresis system, attaching the gel cassette adaptor to the gel cassette to form a gel cassette assembly compatible with a second electrophoresis system, and installing the gel cassette assembly in the second electrophoresis system. In further or alternative embodiment of such methods includes obtaining a gel cassette that is compatible for use with a first electrophoresis system, but which is incompatible for use with a second electrophoresis system; attaching a gel cassette adaptor to such a gel cassette to form a gel cassette assembly that is compatible for use with the second electrophoresis system; and installing the gel cassette assembly in the second electrophoresis system. In further or alternative embodiments of such methods, the gel cassette adaptor comprises an open sided trough having an attachment perimeter and an attachment flange coupled to the attachment perimeter, the attachment flange being configured for compatible mating with the gel cassette. In further or alternative embodiments of such methods, attaching the gel cassette adaptor to the gel cassette forms an upper buffer chamber for the gel cassette assembly. In further or alternative embodiments of such methods, the gel cassette adaptor also includes one or more alignment elements that interact with one or more corresponding features on the gel cassette to facilitate proper positioning of the gel cassette adaptor relative to the gel cassette.

In another aspect are methods of using a single-use gel cassette adaptors described herein, wherein such single-use gel cassette adaptors are used as single-use upper buffer chambers. In further or alternative embodiments such single-use upper buffer chambers contain cathode buffer, while in other embodiments such single-use upper buffer chambers contain anode buffer. In further or alternative embodiments of such methods, the method is a method for performing electrophoresis which includes separating biomolecules using a gel electrophoresis system comprising a gel in electrical communication with a cathode buffer in a single-use upper buffer chamber and an anode buffer in a lower buffer chamber, wherein the gel is in a gel cassette; removing the gel from the gel cassette; and disposing of the single-use upper buffer chamber. In further or alternative embodiments, the single-use upper buffer chamber is a gel cassette adaptor configured for compatible mating with the gel cassette. In further or alternative embodiments of such methods, the gel cassette adaptor includes an open sided trough having an attachment perimeter; and an attachment flange coupled to the attachment perimeter, the attachment flange being configured for compatible mating with the gel cassette. In further or alternative embodiments of such methods, the single-use gel cassette adaptor is between 2 to 10 inches wide×0.5 to 4.0 inch in height×0.5 and 4.0 inches deep, while in further or alternative embodiments, the single-use gel cassette adaptor is between 4 to 8 inches wide×0.75 to 2.0 inch in height×0.75 and 2.0 inches deep. In a further or alternative embodiment, the single-use gel cassette adaptor is approximately 5.4 inches wide×1.3 inches in height×1.1 inches deep. In further or alternative embodiments, the single-use gel cassette adaptor has a volume capacity between about 10 and about 600 mL. In further or alternative embodiments, the single-use gel cassette adaptor has a volume capacity between about 20 and about 400 mL. In further or alternative embodiments, the single-use gel cassette adaptor has a volume capacity between about 30 and about 300 mL. In further or alternative embodiment, the single-use gel cassette adaptor has a volume capacity between 10 and 250 mL. In further or alternative embodiments, the single-use gel cassette adaptor has a volume capacity between about 50 and about 100 mL.

In further or alternative embodiments, the open sided trough and the attachment flange are made of plastic. In further or alternative embodiments, the plastic is an injection molded plastic, while in further or alternative embodiments, the plastic is a thermoformed plastic. In still further or alternative embodiments, the plastic is selected from styrene acrylonitrile, polycarbonate, polystyrene, acrylic based polymers, polymethyl methacrylate, polyethylene terephthalate, glycol-modified polyethylene terephthalate, polypropylene, Acetel and copolymers thereof. In further or alternative embodiments of such methods, the gel cassette adaptor also includes one or more alignment elements that interact with one or more corresponding features on the gel cassette to facilitate proper positioning of the gel cassette adaptor relative to the gel cassette. Further or alternative embodiments of methods of using a single-use gel cassette adaptor include attaching the single-use gel cassette adaptor to a gel cassette to form a gel cassette assembly comprising a gel and an upper buffer chamber; and installing the gel cassette assembly in an electrophoresis system.

In another aspect are methods for generating revenue, comprising selling gel cassette adaptors described herein. In certain embodiments such gel cassette adaptors are used as gel electrophoresis upper buffer chambers. In further or alternative embodiments such gel cassette adaptors are single-use gel cassette adaptors, while in still further or alternative embodiments such single-use gel cassette adaptors are used as gel electrophoresis upper buffer chambers. In further or alternative embodiments, the single-use gel electrophoresis upper buffer chamber includes an open sided trough having an attachment perimeter. In embodiments of this aspect, the trough is between 2 to 10 inches wide×0.5 to 4.0 inch in height×0.5 and 4.0 inches deep, while in further or alternative embodiments, the trough is between 4 to 8 inches wide×0.75 to 2.0 inch in height×0.75 and 2.0 inches deep. In a further or alternative embodiment, the trough is approximately 5.4 inches wide×1.3 inches in height×1.1 inches deep. In further or alternative embodiments, the trough has a volume capacity between about 10 and about 600 mL. In further or alternative embodiments, the trough has a volume capacity between about 20 and about 400 mL. In further or alternative embodiments, the trough has a volume capacity between about 30 and about 300 mL. In further or alternative embodiment, the trough has a volume capacity between 10 and 250 mL. In further or alternative embodiments, the trough has a volume capacity between about 50 and about 100 mL.

Also disclosed herein are gel cassettes having one or more posts that contacts the inner surface of and connects the two gel plates within the domain of the gel. The one or more gel posts stabilize the width of the gap between gel plates to allow rapid high performance electrophoretic separation of biomolecules. In certain embodiments, such gel cassette include a first plate and a second plate arranged in parallel and separated by a gap, wherein the first plate and the second plate are held together along one or more peripheral edges; and at least one gel cassette stabilizer post connecting the first plate to the second plate. In certain embodiments, only a single gel cassette stabilizer post is used. In further or alternative embodiments, the at least one gel cassette stabilizer post is positioned within the top $\frac{1}{3}^{rd}$ of the gel cassette, while in further or alternative, the at least one gel cassette stabilizer post is positioned within the top $\frac{1}{5}^{th}$ of the gel cassette.

In further or alternative embodiments, the at least one gel cassette stabilizer post is centered along the width of the gel cassette, while in still further or alternative embodiments, the at least one gel cassette stabilizer post is positioned within 1 cm of the top of the gel cassette. In further or alternative embodiments, the gel cassette also includes a gel comprising a gel matrix, wherein one or more of the at least one gel cassette stabilizer post is positioned such that it is surrounded on at least three sides by gel matrix. In further or alternative embodiments, the gel cassette also includes a comb, while in further or alternative embodiments, the at least one gel cassette stabilizer post is positioned horizontally between wells formed by the comb. In further or alternative embodiments, the at least one gel cassette stabilizer post is positioned vertically above the level of the bottom of the wells formed by the comb. In further or alternative embodiments, the at least one gel cassette stabilizer post is positioned in an inter-well space. In further or alternative embodiments, the lower edge of the at least one gel cassette stabilizer post is higher than the bottom of the wells of a gel enclosed in the cassette by about 10% or more of the well depth. In further or alternative embodiments, the at least one gel cassette stabilizer post is a series of stabilizer posts. In further or alternative embodiments, the series of gel cassette stabilizer posts are positioned along the width of the gel cassette. In further or alternative embodiments, the gel cassette stabilizer posts are positioned in inter-well spaces.

In further or alternative embodiments, the gel cassette also includes a frame effective for holding the first plate and the second plate along their lateral sides and along the bottom periphery. In further or alternative embodiments, the gel cassette is a wide-format gel cassette. In further or alternative embodiments, the gel cassette is a full size gel cassette. In further or alternative embodiments, the gel cassette is between 4 and 8 inches wide. In further or alternative embodiments, the first plate and the second plate are less than 2.5 mm in thickness.

Also disclosed herein are methods for manufacturing a gel cassette having one or more posts that contacts the inner surface of and connects the two gel plates within the domain of the gel. In certain embodiments such manufacturing methods include holding a first plate and a second plate in parallel orientation separated by a gap using a frame, and connecting a gel cassette stabilizer post to the first plate and/or the second plate. In further or alternative embodiments, the gel cassette stabilizer post is connected to the first plate and/or the second plate using a welding process, or by use of an adhesive. In certain embodiments the welding process is an ultrasonic welding process. In further or alternative embodiments, the gel cassette stabilizer post is formed by a casting process or molding process wherein the at least one stabilizer post is created along with the first plate. In further or alternative embodiments, the gel cassette stabilizer post is formed by a stereolithographic process wherein the at least one stabilizer post is created along with the first plate.

Also disclosed herein are methods for electrophoretically separating one or more biomolecules using an electrophoresis apparatus which includes a gel cassette with at least one stabilizer post. In further or alternative embodiments, such methods include loading a sample comprising one or more biomolecules in a well of a gel enclosed within a gel cassette comprising a first plate, a second plate, and a gel cassette stabilizer post connecting the first plate and the second plate; and applying an electric field to the gel to cause one or more biomolecules to migrate through the gel. In further or alternative embodiments, the gel cassette is a wide format gel cassette. In further or alternative embodiments, the gel cassette is a full size gel cassette. In further or alternative embodiments, the gel cassette is between 4 and 8 inches wide. In further or alternative embodiments, the first plate and the second plate are less than 2.5 mm in thickness. In further or alternative embodiments, the gel cassette is positioned in a gel apparatus designed to hold one or more wide format gel cassettes. In further or alternative embodiments, the gel cassette stabilizer post is positioned above the level of the bottom of the wells. In further or alternative embodiments, the at least one gel cassette stabilizer post is positioned within the top $1/3^{rd}$ of the gel cassette, while in further or alternative embodiments, the at least one gel cassette stabilizer post is positioned within the top $1/5^{th}$ of the gel cassette. In further or alternative embodiments, the at least one gel cassette stabilizer post is centered along the width of the gel cassette, while in still further or alternative embodiments, the at least one gel cassette stabilizer post is positioned within 1 cm of the top of the gel cassette.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

Unless otherwise defined, all technical and scientific terms used herein have the meaning commonly understood by one skilled in the biotechnology art. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description. The following detailed descriptions are merely illustrative in nature and is not intended to limit the invention or the application and uses of the invention. Furthermore, there is no intention to be bound by any expressed or implied theory presented in the preceding technical field, background, brief summary or the following detailed descriptions.

The following detailed description is merely illustrative in nature and is not intended to limit the invention or the application and uses of the invention. Furthermore, there is no intention to be bound by any expressed or implied theory presented in the preceding technical field, background, brief summary or the following detailed description.

Described herein are gel cassette adaptors which may be used to modify electrophoresis gel cassettes, also referred to herein as gel cassettes, to enable their use in alternative electrophoresis systems. The gel cassettes are modified by attaching the gel cassette adaptors to the gel cassette using an adhesive. This attachment may occur outside of the electrophoresis system before placing the modified gel cassette into an electrophoresis system. Alternatively the modification may occur with either the gel cassette already in the electrophoresis system or with the gel adaptor already in the electrophoresis system.

Such gel cassette adaptors described herein may be used as upper or lower buffer reservoirs, and may vary in size and volume capacity depending on the gel cassette and electrophoresis system used. Electrophoresis systems and gel cassettes intended for use with such gel cassette adaptors described herein are generally known to those skilled in the art. In addition, the general construction and operation of gel cassettes are known to those skilled in the art. Although gel cassettes are available in various shapes, sizes, and widths (such as mini-gel cassettes, wide-format gel cassettes, or full size gel cassettes), the invention is not limited to any specific size or configuration of gel cassette 10 or gel cassette assembly. Indeed, one benefit of the gel cassette assembly described herein is that it can be made compatible with a plurality of different electrophoresis systems. The various electrophoresis systems will not be shown or described in detail herein except as necessary in connection with the description of the gel cassette assemblies.

Figure 1:
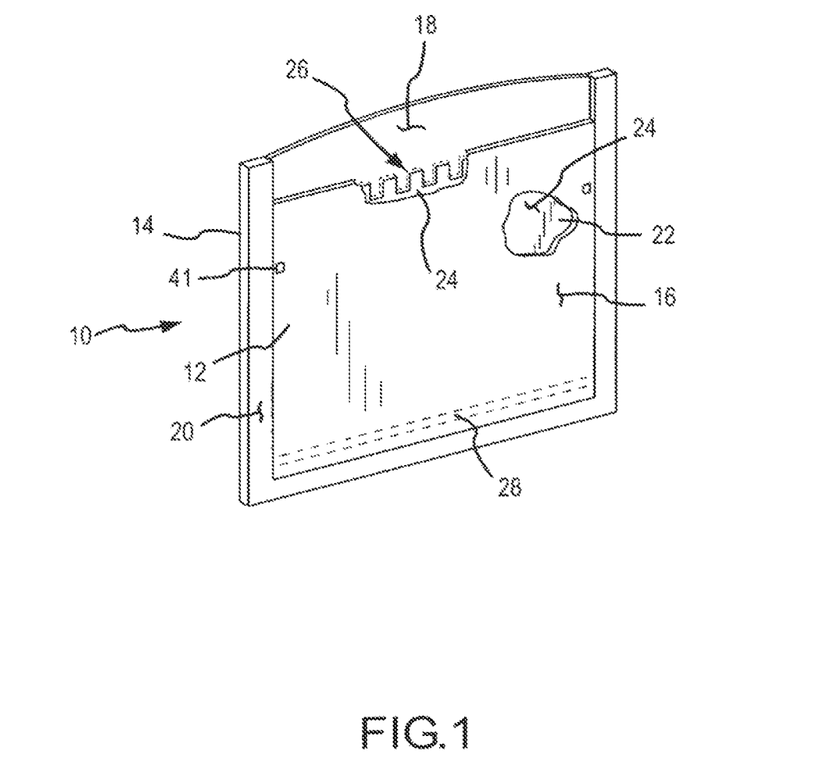
FIG. 1 is a perspective view showing a gel cassette.

FIG. 1 is a perspective view showing one embodiment of a gel cassette 10 that has a front surface 12 and a back surface 14. The gel cassette 10 includes a pair of thin wall plates, including a first plate 16 on the front surface 12, and a second plate 18 on the back surface 14. The first plate 16 (sometimes called the "retainer") is slightly shorter in height than the second plate 18 (sometimes called the "divider"). A frame 20 holds the first plate 16 and second plate 18 along their respective lateral sides and along the bottom periphery to define an internal gel compartment 22 between the plates for holding an electrophoresis gel 24. The gel cassette 10 may be any size used in an electrophoresis system. In typical applications, the gel cassette 10 has a height between about 4 inches (10 cm) and about 8 inches (20 cm) (where height is measured at the outer edges of the cassette) and a width of between about 4 inches (10 cm) and about 8 inches (20 cm). The internal gel compartment that is the gap between assembled plates of the cassette can be from about 0.01 inches (0.25 mm) to about 0.2 inches (5 mm) thick, but is more preferably from about 0.02 inches (0.5 mm) to about 0.12 inches (3 mm) thick, more preferably yet from about 0.04 inches (1.0 mm) to about 0.062 inches (1.5 mm) thick. In one preferred embodiment, the gel cassette is 5.9 inches (15 cm) wide×4.2 inches (10 cm) tall×0.062 inches (1.5 mm) thick. In other preferred embodiments, the cassette is 10 cm wide by 10 cm tall. In some other preferred embodiments, the cassette is 20 cm wide by 15 cm tall. In these embodiments, the internal gel compartment is preferably from about 1 mm to about 1.5 mm thick. The plates of the gel cassette can be 3 mm thick or less, and are preferably 2.5 cm thick or less, for example, 2.2 cm thick or less. In one example, the plates of the gel cassette are 2.2 cm thick in the area of the gel.

Any electrophoresis gel 24 known in the art may be used with gel cassette 10. Gel compartment 22 has a comb opening 26 at the top portion of the gel cassette 10 for receiving a comb for making at least one well 25 which will receive one or more samples to be electrophoretically separated. Located along the lower portion of the second plate 18 and traversing the width of the gel cassette 10 is a lower opening 28 that opens gel compartment 22 to the exterior of the gel cassette 10. In other embodiments, the lower opening 28 may be in the first plate 16 or in both plates. The electrophoresis gel 24 is typically pre-filled within the internal gel compartment 22 for ease of handling. After manufacture of the gel cassette 10, the comb opening 26 is closed with a comb (not shown) and lower opening 28 is masked closed with a removable tape (not shown), which are both removed prior to use.

Figure 2:
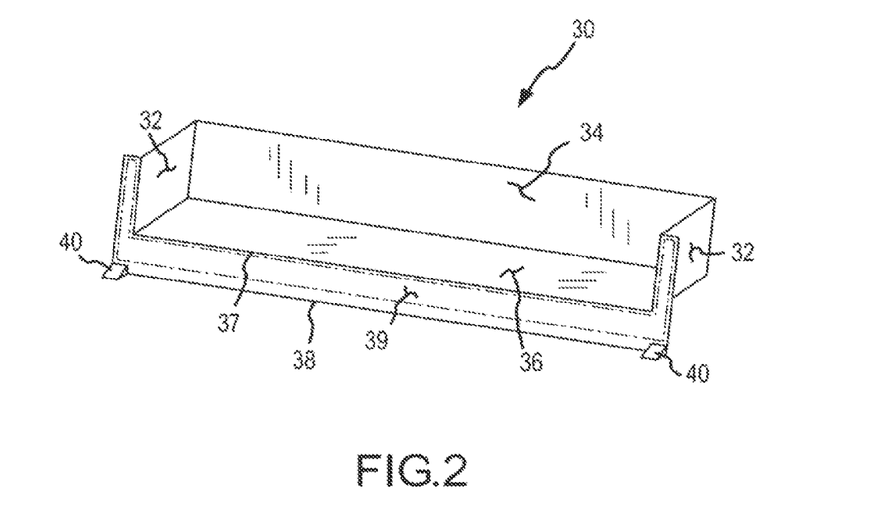
FIG. 2 is a perspective view showing a gel cassette adaptor.

FIG. 2 is a perspective view showing an example gel cassette adaptor 30 for use with a gel cassette 10 for vertical gel electrophoresis, such as the gel cassette 10. The adaptor 30 forms an optionally single-use gel electrophoresis upper buffer chamber when attached to the gel cassette 10 (see FIG. 3). The adaptor 30 is suitably configured to allow gel cassette 10 to be adapted for use in more than one electrophoresis system, as described below. In contrast, conventional gel cassettes are usually only compatible with one (or a limited number of) specific electrophoresis system.

By itself, the gel cassette adaptor 30 is configured as an open sided trough. The open sided trough may be of any size or shape, and the particular configuration may be selected to suit the needs of the given system deployment. By way of example only, gel cassette adaptor 30 shown herein employs a rectangular configuration that includes right and left sides 32, a back side 34, a bottom side 36 and an open front side. The open front side is defined by an attachment perimeter 37, and an attachment flange 38 may be coupled to the attachment perimeter 37. The width of the adaptor 30 may be the same size or smaller than width of the gel cassette 10. By way of example only, the width of the adaptor 30 may be between about 2 inches (5 cm) and about 10 inches (25 cm), or the between about 4 inches (10 cm) and about 8 inches (20 cm). The height and depth of the adaptor may vary depending on the design and volume capacity required in the upper buffer chamber. The height and depth of the adaptor 30 may independently be, by way of example only, between about 0.5 inches (1.3 cm) and about 4 inches (10 cm), or about 0.75 inches (2 cm) and about 2 inches (5 cm). In addition, the volume capacity of adapter 30 may be, by way of example only, between 5 and 1000 mL, between 10 and 600 mL, between 25 and 500 mL, between 20 and 400 mL, between 30 and 300 mL, between 10 and 250 mL, between 50 and 150 mL, or between 50 and 100 mL. A non-limiting example of the adaptor 30, where the gel cassette is 5.9 inches (15 cm) wide×4.2 inches (10.3 cm) tall, the adaptor 30 may be 5.4 inches (13.7 cm) wide×1.3 inches (3.3 cm) in height×1.1 inch (2.8 cm) deep with a 75 mL volume capacity. Furthermore, the adapter, although disclosed herein as an upper buffer chamber in a vertical electrophoresis system, can be a lower buffer chamber and can be used in a horizontal system as a cathode and/or anode buffer chamber.

The attachment perimeter 37 and attachment flange 38 may have various shapes, depending on the configuration of the gel cassette 10 to which the gel cassette adaptor 30 is designed to attach. Thus, in this example, the attachment flange 38 is suitably configured for compatible mating with the gel cassette 10. In some embodiments, gel cassette adaptor 30 may include an adhesive strip or element 39 positioned on the attachment flange 38, the adhesive being configured to facilitate attachment of the gel cassette adaptor 30 to the gel cassette 10. Such adhesive strips include, but are not limited to pressure sensitive tape. A non-limiting example of and adhesive strip is an acrylic based adhesive strip. Alternatively, the gel cassette adaptor 30 may utilize any suitable attachment element, device, or feature, including (without limitation): a glue or other curable adhesive; fasteners; clips; a sealant; a bond or weld; or any combination thereof.

The gel cassette adaptor 30 may also include one or more alignment elements or features that interact with one or more corresponding features on the gel cassette 10 to facilitate proper positioning of the gel cassette adaptor 30 relative to the gel cassette 10. For example, one or more alignment tabs 40 may be positioned on the attachment flange 38, where such alignment tabs 40 are received in one or more retainer notches 41 (see FIG. 1) on the first plate 16. In other embodiments, the first plate 16 or frame 20 may have respective holes, depressions, notches, or other features on the gel cassette 10 to interact with alignment tabs 40.

The gel cassette adaptor 30 is preferably constructed such that a seal is formed around the attachment perimeter 37 when the gel cassette adapter 30 is attached to the gel cassette 10. In addition, the upper buffer chamber formed by the open sided trough is preferably designed to retain fluids without leaking. The gel cassette adaptor 30 may be assembled from multiple pieces or it may be formed as one unitary structure that includes the open sided trough, an integral attachment flange 38 and integral alignment tabs 40.

The gel cassette adaptor 30 may be fabricated from various polymeric materials. Such polymers include, but not limited to, styrene acrylonitrile (SAN), polyurethane, polyvinylchloride (PVC), polycarbonate, polystyrene (PS), acrylic-based polymers, nylon based polymers, polymethylmethacrylate (PMMA), polyethylene terephthalate (PET), glycol-modified polyethylene terephthalate (PETG), polypropylene (PP), cyclo-olefin polymer (COP), polyphenylene ether (PPE), polyoxymethylene (POM), and copolymers thereof. Other representative materials that can be used to fabricate the gel cassette adaptor 30 include, but are not limited to cyclo-olefin copolymer (COC), polychlorotrifluoroethylene (PCTFE), polyetheretherketone (PEEK), polyetherimide (PEI), polyethersulfone (PES), polyethylene (PE), polyethylene naphthalate (PEN), polyester, polyhydroxybutyrate (PHB), polyhydroxyvalerate copolymer, polyimide (PI), polyoxymethylene copolymer (POMC), polyoxymethylene copolymer (POMC), polyoxymethylene homopolymer (POMH), polyphenyleneoxide (PPO), polyphenylenesulfide (PPS), polyphenylsulfone (PPSu), polystyrol, polysulphone (PSu), polytetrafluoroethylene (PTFE), polyvinyl fluoride (PVF), polyvinylidenechloride (PVDC), polybutyleneterephthalate (PBT), fluorinated ethylenepropylene (FEP), perfluoralkoxyalkane (PFA), and polyvinylidenefluoride (PVDF).

The gel cassette adaptor 30 may be fabricated using molding techniques, hot embossing methods, casting processes, thermoforming methods, stereolithography processes, machining methods and milling processes. Such molding techniques include, but are not limited to, injection molded and compression molding. In certain embodiments the gel cassette adaptor 30 may also be machined from a polyoxymethylene copolymer, such as Acetel.

In practice, a gel cassette and a gel cassette adaptor may be included in a gel cassette kit that facilitates conversion of the gel cassette for compatibility with a certain electrophoresis system. For example, the kit may include a gel cassette that is compatible for use with a first electrophoresis system (e.g., a system manufactured by Company A) and is incompatible for use with a second electrophoresis system (e.g., a system manufactured by Company B). In other words, the gel cassette if not modified will still be compatible with the first system. The kit may also include a gel cassette adaptor, as described herein, that is configured for attachment to the gel cassette to convert the gel cassette into a gel cassette assembly that is compatible for use with the second electrophoresis system. In some applications, the conversion process may render the gel cassette assembly incompatible for use with the first electrophoresis system. In other applications, the gel cassette assembly may remain compatible with the first electrophoresis system notwithstanding the conversion. In other embodiments, the gel cassette adaptor 30 may also be provided separately from the gel cassettes 10. For example, a plurality of gel cassette adaptors 30 may be provided in a kit. The kit may also include one or more adhesive strips for attachment of the gel cassette adaptor 30 to gel cassette assemblies.

Figure 3:
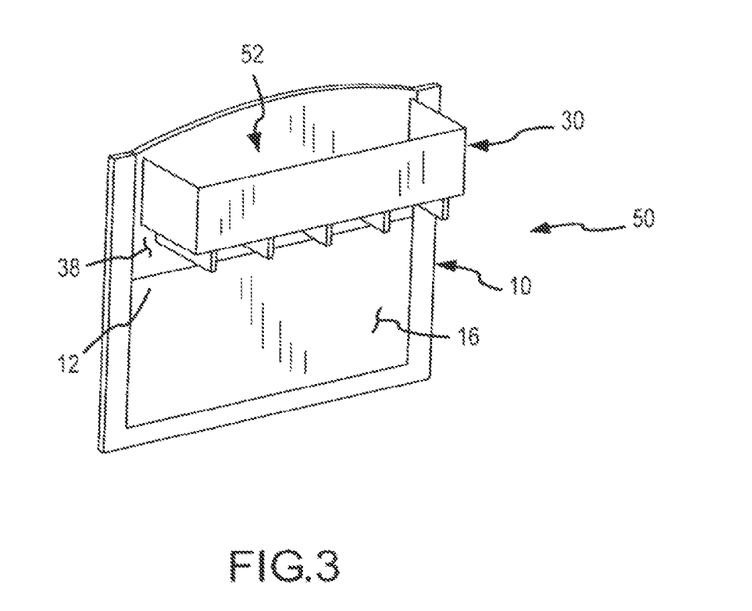
FIG. 3 is a perspective view showing a gel cassette assembly including a gel cassette and a gel cassette adaptor attached thereto.

FIG. 3 is a perspective view showing a gel cassette assembly 50 including a gel cassette 10 and a gel cassette adaptor 30. To assemble the gel cassette assembly 50, an adhesive can be applied to the attachment flange 38 of the gel cassette adaptor 30. Alternatively, an adhesive element or strip 39 covered by an adhesive backing may already be affixed to the attachment flange 38 (see FIG. 1). The gel cassette adaptor 30 is then positioned on the first plate 16 on the front surface 12 of the gel cassette 10, using the alignment tabs 40 to assure proper location and orientation. Enough pressure is applied to sealingly attach the gel cassette adaptor 30 to the gel cassette 10. Once assembled, the gel cassette 10 closes off the front open portion of the gel cassette adaptor 30, forming an upper buffer chamber 52 for the gel cassette assembly 50. In a practical embodiment, the gel cassette adaptor 30 is positioned on the gel cassette 10 such that the comb opening 26 and the wells 25 near the top of the gel cassette 10 are exposed to the upper buffer chamber 52.

In use, a gel cassette is positioned within an electrophoresis system having two buffer solutions, a first buffer solution that is isolated from a second buffer solution. The first buffer solution is introduced into the gel cassette through the comb opening 26 and the second buffer solution has access to the lower opening 28. To keep the first and second buffer solutions separated, they are placed in separate buffer chambers, the first buffer solution being placed in an upper buffer chamber and the second buffer solution being placed in a lower buffer chamber. The upper buffer chamber is in fluid communication with the comb opening 26 and the lower buffer chamber is in fluid communication with the lower opening 28.

Figure 4:
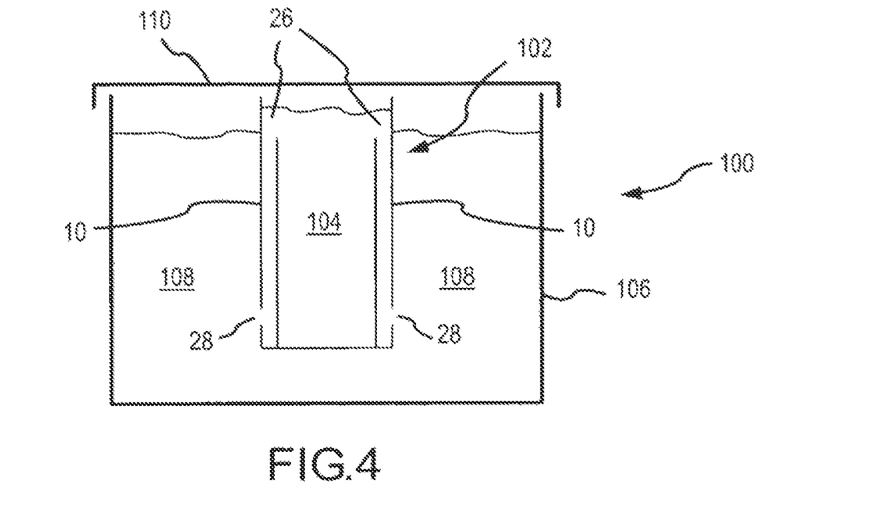
FIG. 4 is a schematic sectional view showing one example of an electrophoresis system in which a gel cassette may be used.

FIG. 4 is a schematic sectional view of an example electrophoresis system 100 in which the gel cassette 10 may be used. FIG. 4 is a side view of the system 100, where the gel cassette 10 is installed in a vertical orientation. In this system 100, two gel cassettes 10 are positioned adjacent to each other with the first sides 12 facing each other in a sandwiched fashion that is sealed along the sides and bottom forming a buffer core assembly 102 having an upper buffer chamber 104. The comb openings 26 near the top of each gel cassette 10 are in fluid communication with the upper buffer chamber 104. The buffer core assembly 102 is placed inside a container 106, and the interior of the container forms a lower buffer chamber 108. The lower openings 28 in the gel cassettes 10 are in fluid communication with the lower buffer chamber 108. In use, the samples to be analyzed are introduced into the gel compartments of the gel cassettes 10 through the comb openings 26 by appropriate means such as a pipette. A first buffer solution is placed in the upper buffer chamber 104 and a second buffer solution is placed in the lower buffer chamber 108. A lid 110 is then positioned in place and the electrophoresis system 100 is assembled and operated by known means. One practical example of an electrophoresis system 100 that uses a buffer core assembly 102 is the XCell SureLock™ Mini-Cell electrophoresis system manufactured by Invitrogen Corporation, of San Diego, Calif.

Figure 5:
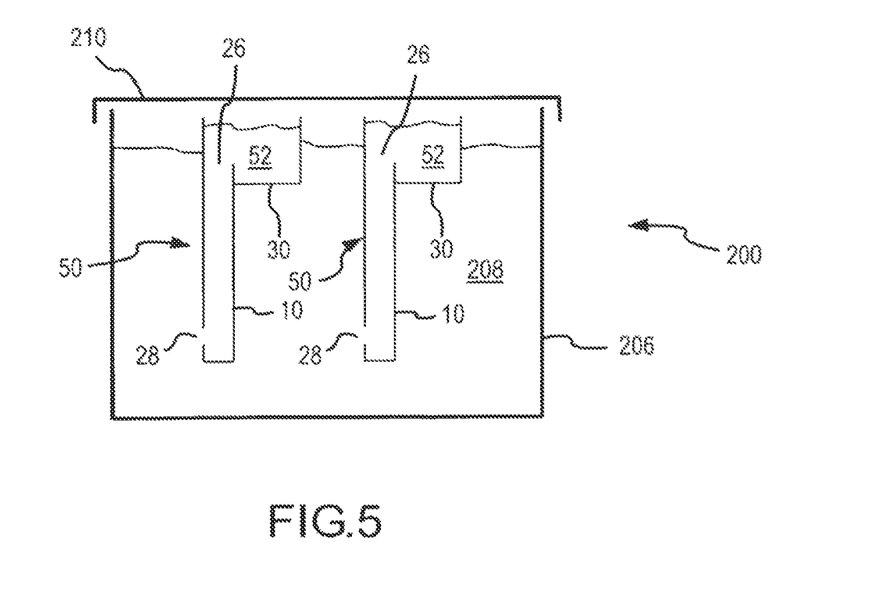
FIG. 5 is a schematic sectional view showing another example of an electrophoresis system in which a gel cassette assembly may be used.

FIG. 5 is a schematic sectional view of an example electrophoresis system 200 in which a gel cassette having an upper buffer chamber is used. For purposes of this description, gel cassettes that are compatible with electrophoresis system 100 are not compatible with electrophoresis system 200. In particular, an unmodified gel cassette 10 would not be compatible with electrophoresis system 200 because it does not have an upper buffer chamber 52. To solve this incompatibility problem, a gel cassette assembly 50 may be used with electrophoresis system 200, where the gel cassette assembly 50 is formed when gel cassette adaptor 30 is applied to the gel cassette 10, thus creating the required upper buffer chamber 52. The comb openings 26 near the top of each gel cassette assembly 50 are in fluid communication with the upper buffer chamber 52. Once assembled, each of the gel cassette assemblies 50 is placed in guide rails inside a container 206, the interior of the container forming a lower buffer chamber 208. Lower openings 28 in the gel cassette assemblies 50 are in fluid communication with the lower buffer chamber 208. In use, the samples to be analyzed are introduced into the gel compartments of the gel cassette assemblies 50 through the comb openings 26 by appropriate means such as a pipette. A first buffer solution is placed in the upper buffer chamber 52 and a second buffer solution is placed in the lower buffer chamber 208. A lid 210 is then positioned in place and the electrophoresis system 200 is assembled and operated by known means. One example of an electrophoresis system 200 that requires gel cassettes having upper buffer chambers described herein is the Criterion™ electrophoresis system manufactured by Bio-Rad Laboratories, of Hercules, Calif.

As described above, an existing gel cassette 10 that is compatible with a first electrophoresis system, such as system 100, may be adapted for use in a second electrophoresis system, such as system 200, by attaching a gel cassette adaptor 30 to the gel cassette 10. In some embodiments, the gel cassette adaptor 30 is a single-use adaptor, such that any stain or protein in the upper buffer chamber is discarded after use. In other embodiments, the gel cassette adaptor 30 may reusable, such that the gel cassette adaptor 30 can be removed from the gel cassette 10 after testing, cleaned, and used again on another gel cassette 10. While the gel cassette adaptor 30 is shown attached to a particular style of gel cassette, other gel cassettes with comparable adaptors would also fall under this invention, and different adaptors can be designed for use with different gel cassettes and different electrophoresis systems.

As discussed above, the gel cassette adaptor 30 forms an upper buffer chamber, and such gel cassette adaptors 30 may be sold separately or in kit form, either in bulk or in combination with a gel cassette 10. In one example, a method for generating revenue comprises selling a disposable or singe use gel electrophoresis upper buffer chamber.

An exemplary method for performing electrophoresis includes separating biomolecules using an electrophoresis system, such as electrophoresis system 200, which comprises a gel in electrical communication with a cathode buffer in a single-use upper buffer chamber described herein and an anode buffer in a lower buffer chamber, the gel being in a cassette, such as gel cassette 10, removing the gel from the cassette, and disposing of the single-use upper buffer chamber described herein.

Figure 8:
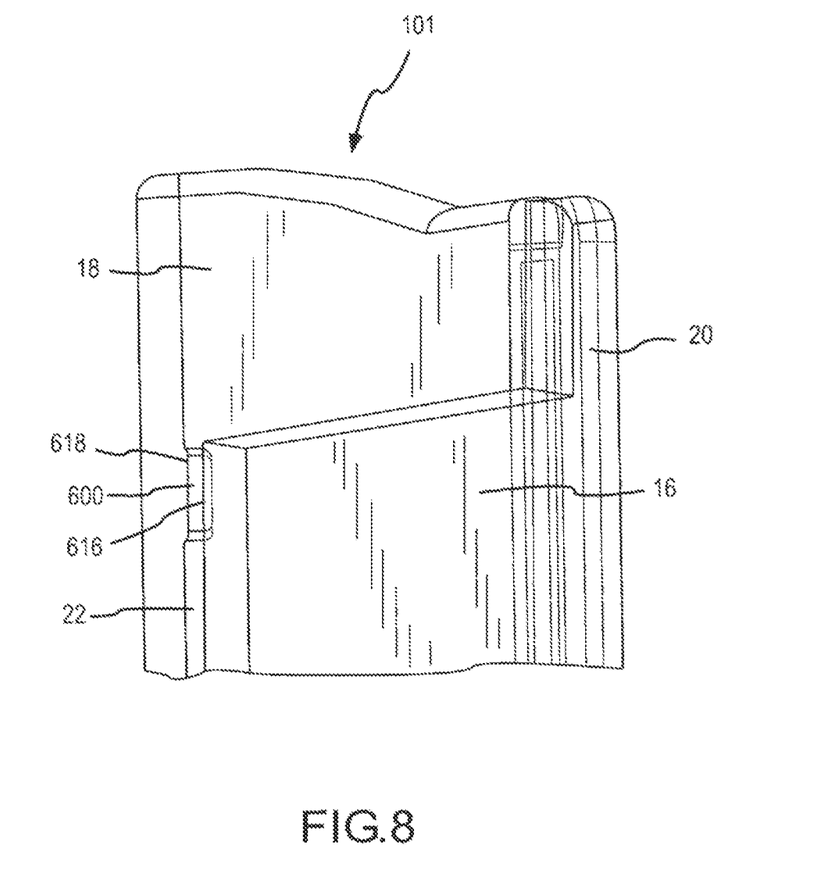
FIG. 8 is a cross-sectional "cut away" view of a mid-section of a cassette having a post attached to the first and second plates.
Figure 9:
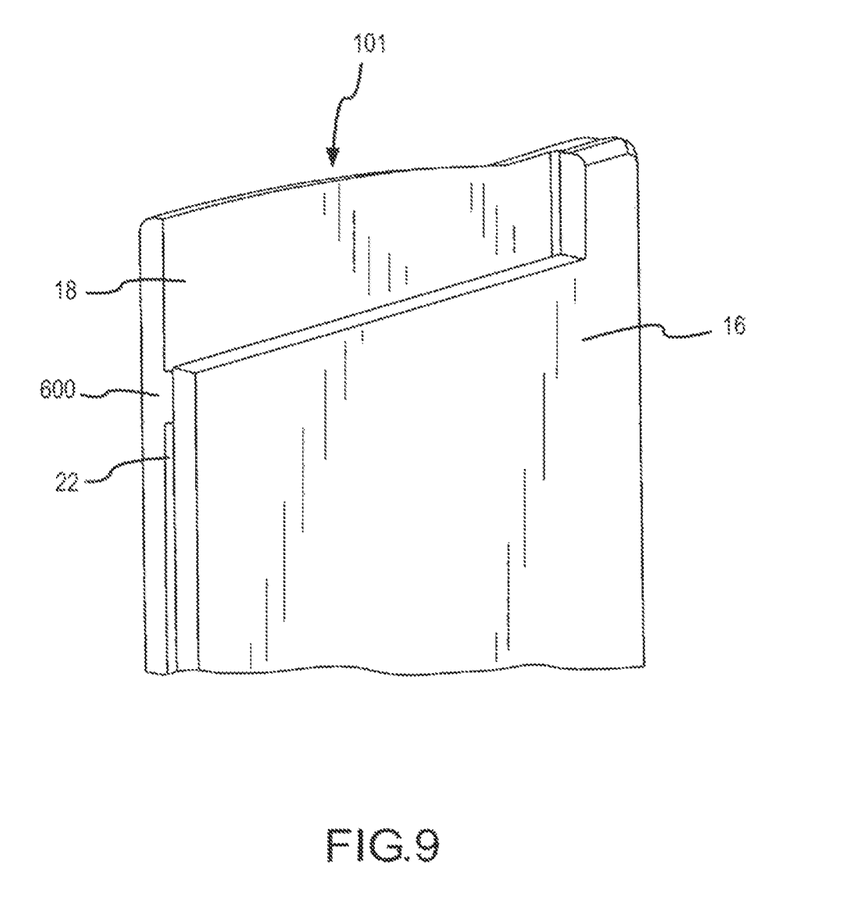
FIG. 9 is a line drawing of a cross-sectional "cut away" view of a mid section of a cassette having a post attached to the first and second plates.

One of the challenges with gel cassette 10 design and operation, depending on the size, thickness, and composition of the gel cassette 10, is that during electrophoresis the gel cassettes can flex from the heat, pressure (such as electro-endoosmotic pressure), and/or other forces inside and outside of the gel thereby altering the gap 22 between plates 16 and 18 of the gel cassette 10 and altering the electrophoretic mobility of biomolecules at different positions along the width of the gel cassette 10. Accordingly, in another embodiment, as shown in FIGS. 8 and 9 that show, for illustrative purposes, one half of a gel cassette, provided herein is a gel cassette 101 that includes a first plate 16 and a second plate 18, arranged in parallel and a gap (i.e. internal gel compartment) 22 that separates the first plate 16 from the second plate 18, wherein the first plate 16 and the second plate 18 are held together along one or more peripheral edges, and wherein the gel cassette 101 further includes a gel cassette stabilizer post 600 that connects the first plate 16 to the second plate 18. The gel cassette 101 in this embodiment of the invention is similar in all ways to the gel cassette 10 disclosed herein, except for the presence of the gel cassette stabilizer post 600 and, in some preferred embodiments, the increased width for a given gel cassette plate (16, 18) thickness that is effectively accommodated as a result of the gel cassette stabilizer post 600. The gel cassette stabilizer post 600 is used to maintain consistent structural stability across the span of the gap (i.e. the internal gel compartment) 22 formed between the first plate 16 and the second plate 18.

Referring to FIG. 8 for illustrative purposes, gel cassette stabilizer post 600 contacts the first plate 16 at a first contact surface 616 and the second plate 18 at a second contact surface 618, where the first contact surface and the second contact surface of a gel cassette stabilizer post are within the domain of the gel. By "within the domain of the gel" is meant that a gel post is positioned so that in an assembled cassette that contains a gel between the plates, where the gel comprises a gel matrix a gel cassette stabilizer post is bordered on at least three sides by gel matrix. In some embodiments, a gel cassette stabilizer post is bordered on all four sides by gel matrix, where "all four sides" refers to two sides in the width dimension and two sides in the length dimension of the gel. In some embodiments, electrophoresis of one or more biomolecules can occur on either side (in the width dimension) of at least one stabilizer post used in a gel cassette having one or more gel cassette stabilizer posts. The gel matrix is not limiting, and can include, for example, an acrylamide, agarose, or any other polymer suitable for electrophoresis, including combinations and mixtures of acrylamide, agarose, or other polymers.

The gel cassette stabilizer post 600 provides stability in both tensile and compressive directions to heat, pressure (for example electro-endoosmotic pressure), and other forces that can act on the cassette 101 during electrophoresis. Furthermore, the gel cassette stabilizer post 600 helps to assure that there is an acceptably consistent gap 22 between the first plate 16 and the second plate 18 across the span of the gel cassette 101 during electrophoresis. In addition, the gel cassette stabilizer post 600 allows the manufacture of gel cassettes 101 with greater width while using thinner plate material than is possible without the gel cassette stabilizer post 600 or without using sophisticated and more costly manufacturing methods. In certain illustrative examples, the gel stabilizer post 600 does not form all or any external boundary portion of a spacer between a well.

The gel cassette stabilizer post 600 can be located on a variety of points both with respect to the top (i.e height) of the gel cassette 101 and the sides (i.e. width) of the gel cassette 10. A gel cassette stabilizer post can be positioned optimally by determining a region or regions most in need of structural reinforcement during electrophoresis. In most cases, localization of a gel cassette stabilizer post will be to a position farthest from other plate-to-plate contacts, which in some preferred embodiments are at the perimeter of the sides and bottom of the cassette where the plates connect or are held to one another (for example, at the frame). In this case, a preferred embodiment has a single post positioned centrally in the gel cassette with respect to the width dimension (approximately midway between the sides of the cassette, where the plates are anchored to one another by the frame) and in the upper third of the gel cassette with respect to the length dimension (close to the top, where there are no plate-to-plate connections). However, where more than one post is employed, the posts can be distributed to stabilize the gap between plates by spacing them, for example, along the width or in any region of the upper third of the cassette, along the width or in any region of the upper half of the cassette, or lower, to prevent or reduce deformation of the gap width at any part of the cassette during electrophoresis.

Optimal positioning of one or more posts positioned to reduce gap deformation will depend on the position and strength of the attachments of the plates to one another, and the possible attachment of either or both of the plates to one or more other reinforcing structures and the position and strength of such attachments. The spacing of multiple posts can be any spacing that reduces changes in gap width during electrophoresis, and can include positioning of posts at different heights or distances from the side edges of the cassette, where the spacing between multiple posts can be even or uneven. The optimal positioning of the posts can be assisted by determining the region of maximal deformation of the inner gel space during electrophoresis. This can be performed, for example, using laser measurements along the cassette at timed intervals (e.g., every minute) during an electrophoresis run. Such measurements can show the deflection of the cassette in one or more regions and thereby indicate the region of the cassette requiring reinforcement.

Figure 6:
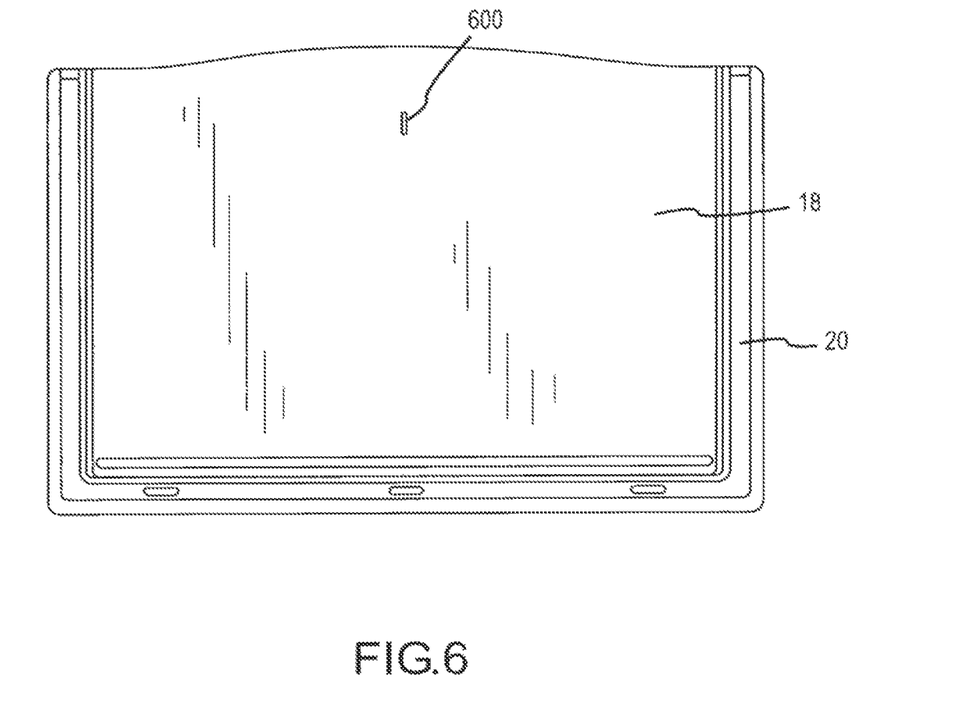
FIG. 6 is a schematic face-on view of the second plate or "divider" having a single post attached to the center of the upper third of the plate.

In embodiments such as those depicted in FIGS. 6, 8, and 9, the gel cassette includes a frame 20 that connects the two plates 16, 18 at the perimeter of the sides and bottom of the plates 16, 18. In this embodiment, the gel cassette stabilizer post 600 is positioned within a central $1/3^{rd}$, preferably $1/4^{th}$, and most preferably $1/5^{th}$ region, of the gel cassette 101 with respect to the width of the gel cassette 101. In preferred embodiments in which a single gel cassette stabilizer post 600 is used, the gel cassette stabilizer post 600 is centered along the width of the gel cassette 101. With respect to its placement along the height of a gel cassette 101, the gel cassette stabilizer post 600 can be positioned in the top $1/2$ of the gel cassette 101, within the top $1/3^{rd}$, $1/4^{th}$, or $1/5^{th}$ of the gel cassette. In specific non-limiting examples, it is positioned within 3, 2, or 1 cm of the top of the gel cassette 101.

In some designs, the upper edge of a post can be at the upper edge of the shorter of the two gel plates (16 in FIGS. 8 and 9) of a cassette. In other designs, the upper edge of a post can be below the upper edge of the shorter of the two gel plates of a cassette.

Furthermore, a gel cassette stabilizer post 600 is typically positioned such that when a gel is formed in the cassette, the post will be within the space between wells (inter-well spaces) formed by a comb that fits the cassette or directly below the spaces formed by a comb positioned within the gel cassette 101 (or partly within and partly directly below a space), so as not to interfere with the migration of biomolecules within the gel cassette 101. Regardless of the height of the post with respect to the wells, the post is surrounded by gel matrix on at least three sides when a gel is within the cassette. A gel cassette stabilizer post does not form the sides of a well, but can be positioned in alignment with an inter-well space to avoid interference with electrophoresis of samples loaded in the wells. Thus, positioning of a post can include determining the positions of wells that will be formed by one or more combs inserted into the cassette, such that a gel cassette stabilizer post is horizontally positioned between wells formed by one or more combs that can be inserted into a cassette when forming the gel, and a gel cassette stabilizer post can optionally be positioned vertically above the level of the bottom of wells formed by a comb.

One or more posts can be positioned above the level of the bottom of the wells of a gel enclosed within the cassette. A preferred design for a gel cassette is a cassette having one or more posts positioned such that when the cassette holds a gel having wells, the post is positioned in a portion of the gel that is between two wells (an inter-well space) and above the level of the bottom of the wells, and in the center of the gel with respect to width. For example, one or more gel cassette stabilizer posts can be positioned such that each is in an inter-well space such that its lower edge is higher than the bottom of the wells of a gel enclosed in the cassette by about 10% or more of the well depth, by about 20% or more of the well depth, by about 30% or more of the well depth, by about 40% or more of the well depth, or by about 50% or more of the well depth. In these designs it is preferred that a cassette that holds a get having wells has fewer posts than inter-well spaces, and in certain illustrative examples, there are 5 posts, 4 posts, 3 posts, 2 posts, or 1 post.

In an exemplary design, a gel cassette includes a single gel cassette stabilizer post that is positioned in or below an inter-well space in the upper one-half of the gel cassette, preferably the upper one-third of the gel cassette, or positioned in an inter-well space such that its lower edge is higher than the bottom of the wells of a gel enclosed in the cassette by about 10% or more of the well depth, by about 20% or more of the well depth, by about 30% or more of the well depth, or by about 40% or more of the well depth.

In another example, a gel cassette can be from 10 cm to 20 cm wide and from 10 cm to 20 cm in height, and one or more gel cassette stabilizer posts can be positioned such that each post is in an inter-well space such that the lower edge of the post is higher than the bottom of the wells of a gel enclosed in the cassette (or the teeth of a comb that fits the cassette and can be used in forming a gel) by about 1 mm or more, by about 2 mm or more, by about 3 mm or more, by about 4 mm or more, or by about 5 mm or more. In particular designs, a gel cassette is located in the top one-half, preferably top one-third of the gel cassette 10, and includes fewer stabilizer posts than wells, for example, 2, 3, 4, or 5, fewer stabilizer posts than wells, or for example, 1 to n−1, n−2, n−3, n−4, n−5, n−6, n−7, n−8, n−9, n−10, n−11, n−12, n−13, n−14, n−15, n−16, n−17, n−18, n−19 etc. stabilizer posts, wherein n is the total number of wells and at least 1 stabilizer post is present. In some examples, a gel cassette can enclose a gel having 10 or more wells and 5 or fewer posts, such as 5 posts, 4 posts, 3 posts, 2 posts, or, preferably, a single post. In an illustrative example, a gel cassette includes a single gel cassette stabilizer post that is positioned in an inter-well space such that its lower edge is higher than the bottom of the wells of a gel enclosed in the cassette (or the teeth of a comb that fits the cassette and can be used in forming a gel) by about 1 mm or more, by about 2 mm or more, by about 3 mm or more, by about 4 mm or more, or by about 5 mm or more. Furthermore, in certain illustrative examples, there are no stabilizer posts present in the bottom one-half of the gel cassette. In addition, in one example one stabilizer post is positioned near the center of the gel with respect to both vertical and horizontal orientation.

In another embodiment, one or more posts are positioned in inter-well spaces such that the lower edge of a post is below the level of the bottom of the wells of a gel enclosed within a cassette. The upper edge of a post can align with the upper edge of the first (retainer) plate 16 and the tops of the wells formed by a comb, or alternatively can be below the level of the upper edge of the first (retainer) plate 16 and the tops of the wells formed by a comb. In another embodiment, one or more posts are positioned such that they are entirely below the level of the bottom of the wells. These parameters are guidelines only, and refer particularly but not exclusively to designs such as that depicted in FIGS. 6, 8, and 9, in which the cassette 101 has anchor points at the frame 20 that attaches the first and second plates (16 and 18) to one another.

In some aspects, a gel cassette further includes a separate frame 20 that is effective for holding the first plate and the second plate along their lateral sides and/or along the bottom periphery. The frame can include a spacer that determines the thickness of the gap between plates 22. In other preferred aspects, however, the frame 20 is not a separate piece, but a region of the cassette formed by the periphery of the sides and bottom of first and second plates that attach a first plate to a second plate, such as by one or more interlocking ridges and grooves on the peripheries of the plates. The plates are configured such that when they interlock, a particular gap width is established between the first plate 16 and second plate 18. Accordingly, in these embodiments the first plate 16 and the second plate 18 are held together by both the frame 20 and the gel cassette stabilizer post 600.

The gel cassette 101 can be virtually any size known in the gel electrophoresis arts. In some examples, gel cassettes 101 may range from about 10 cm (4 inches) to about 20 cm (8 inches) wide and about 10 cm to about 20 cm high. However, in preferred embodiments, the gel cassette 101 is wider than a mini-gel cassette (10 cm). In one specific illustrative example, the gel cassette 101 is a wide-format gel cassette, meaning it has a width of greater than 15 cm. For example, a wide format gel cassette can be from about 15 cm to 20 cm or more in width. In another specific illustrative example, the gel cassette 101 is a full size gel cassette 101 that can be 20 cm or greater in width. Typical dimensions for gel cassettes that can include one or more stabilizer posts include the mini-gel cassette size of 10 cm wide×10 cm high (where height is measured at the side edges of the cassette), the midi-gel cassette size of 15 cm wide×10 cm high (where height is measured at the side edges of the cassette), and the full size gel cassette which can be 20 cm wide×15-20 cm high (where height is measured at the side edges of the cassette). Such cassette sizes are not limiting, however, as a gel cassette stabilizer post can provide advantages in gel cassettes of a wide range of sizes.

The presence of one or more gel cassette stabilizer posts 600 can allow the first plate 16, the second plate 18, or both to be thinner than is otherwise possible while providing acceptable electrophoretic performance during electrophoresis. For example, use of one or more gel cassette stabilizer 600 posts can allow the use of thinner plate materials (such as, but not limited to, plastics or polymers) than can be used in the absence of one or more cassette posts 600, since the deformation of the gap 22 between plates 16 and 18 during electrophoresis depends, in part, on the strength, and therefore the thickness, of the plate material. Depending on the material used to make the first plate 16 and second plate 18 of the cassette 101, the width of the cassette, and the size and number of posts employed, gel plates can be, for example, 3 mm thick or less, more preferably 2.5 mm thick or less, or even more preferably, 2.2 mm thick or less. In an exemplary embodiment of the present invention in which the cassette 101 is 15 cm wide by 10 cm high, and the first and second plates (16 and 18) of the cassette 101 are held together at frame 20 at the bottom and side edges of the cassette, and connected by a single post 600 having an area of 0.0125 cm$^2$ positioned (with respect to the second, or divider plate 18) as shown in FIG. 6, and the cassette plates are made of clear SAN plastic, the plates are 2.2 mm thick in the region of the gel. The inventors have found that using a single gel cassette stabilizer post 600 as provided herein, gap deformation during electrophoresis of proteins in acrylamide gels was minimized. The inventors have found that without the gel cassette stabilizer post 600 provided herein, a consistent gap 22 was not maintained for the described cassette during electrophoresis.

One or more than one gel cassette stabilizer post 600 can be used in gel cassettes according to this embodiment of the invention. For example a series of gel cassette stabilizer posts 600 can be used. The series is typically 10 or fewer gel cassette stabilizer posts 600. In specific examples, 25, 20, 15, 14, 13, 12, 11, 10, 9, 8, 7, 6, 5, 4, 3, 2, or 1 gel cassette stabilizer post 600 can be used. Typically, the gel cassette stabilizer post(s) 600 are evenly spaced along the width of the cassette. A preferred design of a cassette having one or more stabilizer posts is a cassette that has fewer stabilizer posts than inter-well segments. In general, fewer gel cassette stabilizer posts 600 are preferred due to lower costs due to less material and easier manufacturing, and because of less interference with comb placement, sample loading, and biomolecular migration. Therefore, in some preferred embodiments in which the cassette 101 comprises a frame 20 that holds the plates together at the sides and bottom of the cassette 101, a single gel cassette stabilizer post 600 is utilized that is located at or near the center with respect to the width of the first plate 16 and/or the second plate 18. Preferred designs of cassettes are shown in FIGS. 8 and 9, where the cassettes have a single stabilizer post 600.

The gel cassette stabilizer post 600, can be virtually any size or shape provided that it sufficiently holds together the first plate 16 and the second plate 18, and does not interfere with sample comb placement, sample loading, or biomolecule migration during electrophoresis. The shape of the gel cassette stabilizer post 600 can be virtually any shape provided that it meets the functional characteristics provided herein. For example, in cross section, the shape of the first contact surface 616 and/or the second contact surface 618 can be circular, oval, square, rectangular, triangular, hexagonal, octaganoal, or irregular, and even in cross-sectional shapes that include straight lines, the shape can include one or more rounded edges (e.g., rod shaped). Furthermore, where the first contact surface 616 and/or the second contact surface 618 do not have the same dimensions on all sides, the contact surfaces are preferably longer than they are wide (where length and width are used in the same sense as for the cassette, i.e, length is the direction that electrophoresis occurs in) to cause less interference with comb placement, sample loading, and biomolecule migration. In an illustrative example, as shown in FIGS. 6, 8, and 9, the post has an elongated rod shape on a first contact surface 616 and on a second contact surface 618.

Referring to FIG. 8, the first contact surface 616 and the second contact surface 618 typically each have an area of less than 1 cm$^2$, and in certain preferred embodiments have a surface area of less than 0.5, 0.25, 0.1, 0.05, or 0.02 cm$^2$. For example, in a preferred embodiment depicted in FIGS. 6, 8, and 9, the cassette is a wide format cassette having a width of 15 cm and a height (at the edges) of 10 cm, and having a single post positioned in the center of the cassette in the width dimension, and in the top $5^{th}$ of the cassette in the length dimension (just below the upper edge of the first plate), and the post has a first contact area and a second contact area of about 0.0125 cm$^2$.

Furthermore, the surface area of each of the first contact surface 616 and the second contact surface 618, in certain embodiments is no larger than $\frac{1}{100}^{th}$, and preferably $\frac{1}{250}^{th}$, more preferably $\frac{1}{500}^{th}$, and most preferably not larger than $\frac{1}{1000}^{th}$ of the surface area of the first plate 616 and the second plate 618. The gel cassette stabilizer post 600 typically extends between the first plate 616 and the second plate 618 the same distance as the depth of the internal gel compartment or gap 22 between the first plate 616 and the second plate 618.

The surface area of a gel stabilizer post will depend on the electrophoresis conditions used, including but not limited to, the electrophoresis buffer, the gel composition, and the applied voltage, the thickness of the first and second plates, the number of posts, and the distance from anchor point to anchor point, where an anchor point is a point at which there is plate to plate contact (such as at the frame, for example) or one or both plates are connected to a stabilizing structure (such as a part of the gel apparatus). In many cases, the distance from anchor point to anchor point will be, in one dimension, the width of the gel, and in another dimension the height of the gel.

There may, however, be differently positioned anchor points for a given cassette gel apparatus configuration that can be taken into account when determining a position of a cassette requiring reinforcement by one or more posts. For example, in some gel apparatus designs, the upper region of the cassette may be secured at one or more points to a structure of the gel apparatus during electrophoresis, providing additional anchor points at the upper region of the cassette. In addition, where more than one post is employed, an anchor point can be another post. Determination of the effectiveness of a gel stabilizer post in preserving gap width during electrophoresis can be by measuring the gap width using a laser, or by evaluating the resolution of gel bands after electrophoresis. The surface area of a gel stabilizer post can be increased or decreased as necessary so that it preserves gap width but minimally interferes with spacing of gel lanes and electrophoresis of biomolecules.

The gel cassette stabilizer post 600 can be made of virtually any material that does not interfere with the migration of biomolecules in the gel during electrophoresis and does not degrade a gel or otherwise negatively affect a gel located within a gel cassette 10. In preferred embodiments, the gel cassette stabilizer post 600 is made of a plastic material and in preferred embodiments is made of the same plastic that is used for the first plate and or the second plate. The gel cassette stabilizer post 600 may be fabricated from various polymeric materials. Such polymers include, but not limited to, styrene acrylonitrile (SAN), polyurethane, polyvinylchloride (PVC), polycarbonate, polystyrene (PS), acrylic-based polymers, nylon based polymers, polymethylmethacrylate (PMMA), polyethylene terephthalate (PET), glycol-modified polyethylene terephthalate (PETG), polypropylene (PP), cyclo-olefin polymer (COP), polyphenylene ether (PPE), polyoxymethylene (POM), and copolymers thereof. Other representative materials that can be used to fabricate the gel cassette adaptor 30 include, but are not limited to cyclo-olefin copolymer (COC), polychlorotrifluoroethylene (PCTFE), polyetheretherketone (PEEK), polyetherimide (PEI), polyethersulfone (PES), polyethylene (PE), polyethylene naphthalate (PEN), polyester, polyhydroxybutyrate (PHB), polyhydroxyvalerate copolymer, polyimide (PI), polyoxymethylene copolymer (POMC), polyoxymethylene copolymer (POMC), polyoxymethylene homopolymer (POMH), polyphenyleneoxide (PPO), polyphenylenesulfide (PPS), polyphenylsulfone (PPSu), polystyrol, polysulphone (PSu), polytetrafluoroethylene (PTFE), polyvinyl fluoride (PVF), polyvinylidenechloride (PVDC), polybutyleneterephthalate (PBT), fluorinated ethylenepropylene (FEP), perfluoralkoxyalkane (PFA), and polyvinylidenefluoride (PVDF).

The gel cassette stabilizer post 600 may be fabricated using molding techniques, hot embossing methods, casting processes, thermoforming methods, stereolithography processes, machining methods and milling processes. Such molding techniques include, but are not limited to, injection molded and compression molding. In certain embodiments the gel cassette stabilizer post 600 may also be machined from a polyoxymethylene copolymer, such as Acetel.

Figure 7:
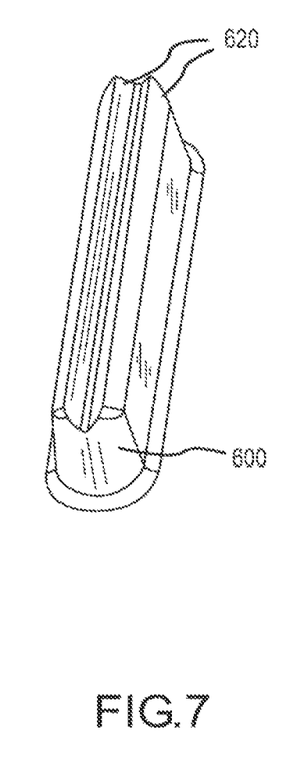
FIG. 7 is a schematic depiction of one design of a post prior to attachment to a gel cassette.

As will be understood, many different methods of joint design can be used to connect the gel cassette stabilizer post 600 to the first plate 16 and the second plate 18. Therefore, provided herein is an exemplary method for manufacturing a gel cassette, that includes holding a first plate 16 and a second plate 18 in parallel orientation separated by a gap 22 using a frame 20, and connecting a gel cassette stabilizer post 600 to the first plate 16 and/or the second plate 18. The gel cassette stabilizer post 600 can be connected to the first plate 16 and/or the second plate 18 using a welding process. By way of example only, a gel cassette stabilizer post 600 can be ultrasonically welded to the first plate 16 and/or the second plate 18. One specific example of a gel cassette stabilizer post 600 for use with an ultrasonic welding process is illustrated in FIG. 7. In this example, the gel cassette stabilizer post 600 can be cast in a mold of either the first plate 16 or the second plate 18, and then ultrasonically welded to the other plate. The gel cassette stabilizer post 600 can include 2 energy directors 620 at the top to initiate plastic melt to allow the gel cassette stabilizer post 600 to be joined to the plate to which it is not formed during the plastic casting process.

Other means of attachment of a post to a cassette can also be used, providing that the attachment is durable so that the post does not dissociate from either plate during electrophoresis. For example, a gel cassette stabilizer post can be molded as part of either a first or a second plate, and attached by an adhesive to the opposite plate. Alternatively, a portion of a post can be molded as part of each of a first and second plate, and the two portions attached to their respective plates can be attached by welding or by adhesives. In yet other embodiments, a portion of a post can be molded as part of each of a first and second plate, where the two portions can be connected by a joint, snap, or other connector, such as, for example, an interference connector that can form a tight junction.

The invention also provides methods of electrophoretically separating one or more biomolecules, where the method includes: loading one or more samples that include one or more biomolecules in a well of a gel enclosed within a gel cassette that includes a first plate and a second plate, and one or more gel cassette stabilizer posts connecting the first plate and the second plate, and applying an electric field to the gel, where the electric field causes the migration of the one or more biomolecules through the gel.

In using a gel cassette that has one or more stabilizer posts for electrophoresis of biomolecules, the cassette can be used in any of a wide variety of gel apparatuses that provide electrodes, electrode connections, and buffer reservoirs, and a supporting structure that can hold a gel cassette, or to which a gel cassette can be attached. In a preferred embodiment, the cassette is positioned in a gel apparatus that can hold one or more wide format gel cassettes, that is, cassettes having a width of 15 cm or greater. The apparatus can be designed to hold one or more than one cassette for electrophoresis. A wide variety of electrophoresis methods are known in the art, varying, for example, in gel composition (for example, acrylamide, agarose, or combinations thereof), gel concentration (gels can be of a uniform concentration or can have regions of different concentration of the gel matrix or can have a gradient of concentrations), buffer composition and concentration, the presence of detergents, denaturing agents, ampholytes, buffers, salts, reducing agents, antioxidants, substrates, chelators, etc. in the gel or buffer, buffer volume, the applied voltage, running current, etc. In addition, sample preparation and sample buffer composition can vary according to various protocols known in the art and as optimized and altered by practitioners.

The gel cassette and apparatus modifications disclosed herein, including the adaptor and gel cassette stability post, are not limited in their use to particular electrophoresis techniques, protocols, compositions, or apparatuses. For example, a gel cassette that includes one or more gel stability posts can be used in a gel apparatus that can accommodate one or more cassettes having a width of greater than 10 cm, where the gel comprises acrylamide with or without detergent (e.g., SDS). Electrophoresis can be performed using any suitable running buffer, such as, for example, Tris-glycine, Bistris, Tris-acetate, Tris-borate, etc. The samples can be crude fractions or lysates of cells, tissues, or biological or environmental samples, or can be partially or substantially purified biomolecules, such as, but not limited to, proteins or nucleic acids.

Electrophoresis can be performed at one or more voltages or at one or more current values. For example, electrophoresis can be performed at from about 2 milliAmps to about 300 milliAmps, preferably from about 4 milliAmps to about 150 milliAmps, and more preferably from about 5 milliAmps to about 100 milliAmps. Electrophoresis can be performed at, for example, from about 10 to about 1,000 Volts, preferably from about 20 to 500 Volts, and more preferably from about 50 to about 250 Volts. In some preferred embodiments, voltage can be held constant, and optionally changed, for example, from one constant voltage to another constant voltage, for one or more time periods during the electrophoresis run. By way of example only, the applied voltage may be pulsed between set voltage values, the applied voltage may be ramped in a staircase mode from high voltage to low voltage, the applied voltage may be ramped in a staircase mode from low voltage to high voltage, the applied voltage may be continuously ramped from high voltage to low voltage, or the applied voltage may be continuously ramped from low voltage to high voltage.

In inhibiting deformation of the gap between gel plates, one or more gel cassette stabilizer posts can allow for using increased voltage and faster electrophoresis runs than can be performed in analogous systems lacking a gel cassette stabilizer post, since resolution of gel bands is not adversely affected by gap distortion that can occur in the absence of the post.

Electrophoresis can be performed for a sufficient time to resolve and separate biomolecules of interest. This depends in part on factors such as the size of the biomolecules to be separated, the size of the gel, and the gel concentration. The time frame can be on the order of from minutes to hours. For example, electrophoresis of a 4-20% gradient acrylamide gel having a height of about 10 cm can be from 15 minutes to five hours, more preferably from 20 minutes to 3 hours.

Preferably, during the course of electrophoresis, at least one of the biomolecules being separated migrates past a gel cassette stabilizer post. In some preferred embodiments, one or more gel cassette stabilizer posts is positioned in the upper one third of the cassette, and at least one of the biomolecules being separated migrates past the one or more gel cassette stabilizer posts. In some preferred embodiments, one or more gel cassette stabilizer posts is positioned in the upper one fifth of the cassette, and at least one of the biomolecules being separated migrate past the one or more gel cassette stabilizer posts. In some preferred embodiments, one or more gel cassette stabilizer posts is positioned in the upper one cm of the cassette, and all of the biomolecules being separated migrate past the one or more gel cassette stabilizer posts.

While at least one example embodiment has been-presented in the foregoing detailed description, it should be appreciated that a vast number of variations exist. It should also be appreciated that the example embodiment or embodiments described herein are not intended to limit the scope, applicability, or configuration of the invention in any way. Rather, the foregoing detailed description will provide those skilled in the art with a convenient road map for implementing the described embodiment or embodiments. It should be understood that various changes can be made in the function and arrangement of elements without departing from the scope of the invention as set forth in the appended claims and the legal equivalents thereof.

All patents, patent publications, patent applications and other published references mentioned herein are hereby incorporated by reference in their entirety as if each had been individually and specifically incorporated by reference herein.

What is claimed is:

1. A gel cassette comprising:
A first plate and a second plate arranged in parallel and separated by a gap, where in the first plate and the second plate are held together along one or more peripheral edges; and
a single gel cassette stabilizer post connecting the first and second plate and positioned within the top $1/3^{rd}$ of the gel cassette without the post contacting any peripheral edge of the first or second plate, so that gel could be formed to substantially encircle the post.

2. The gel cassette of claim 1, wherein said stabilizing post is coupled to an inner surface of at least the first or the second plate and positioned within the gap separating the first plate and the second plate.

3. The gel cassette of claim 1, wherein the gel cassette stabilizer post is positioned within the top $1/5^{th}$ of the gel cassette.

4. The gel cassette of claim 1, wherein the gel cassette stabilizer post is positioned within 1 cm of the top of the gel cassette.

5. The gel cassette of claim 1, further comprising a gel matrix which further comprises plurality of wells.

6. The gel cassette of claim 1, wherein the gel cassette stabilizer post is positioned in an inter-well space.

7. The gel cassette of claim 6 wherein the gel cassette stabilizer post is positioned in one of the inter-well spaces.

8. The gel cassette of claim 5, wherein the lower edge of the gel cassette stabilizer post is higher than the bottom of the wells of a gel enclosed in the cassette by about 10% or more of the well depth.

9. The gel cassette of claim 1, further comprising a frame effective for holding the first plate and the second plate along their lateral sides and along the bottom periphery.

10. The gel cassette of claim 1, where in the gel cassette is a wide-format gel cassette.

11. The gel cassette of claim 1, wherein the gel cassette is a full size gel cassette.

12. The gel cassette of claim 1, wherein the gel cassette is between 4 and 8 inches wide.

13. The gel cassette of claim 1, wherein the first plate and the second plate are less than 2.5 mm in thickness.

14. The gel cassette of claim 1, further comprising a comb.

* * * * *